US008355962B2

(12) United States Patent
Delaney et al.

(10) Patent No.: US 8,355,962 B2
(45) Date of Patent: Jan. 15, 2013

(54) PRODUCT STORAGE AND RETRIEVAL SYSTEM

(75) Inventors: Kevin C. Delaney, San Jose, CA (US); Robert G. Guillermo, Milpitas, CA (US); Kendrick S. Lim, Dublin, CA (US); Roy G. Ponferrada, Santa Clara, CA (US); William S. Cras, Alamo, CA (US); Richard M. Lee, Volcano, CA (US); David A. Victoria, Blackton, CA (US)

(73) Assignee: PickPoint Corporation, Pleasanton, CA (US)

( * ) Notice: Subject to any disclaimer, the term of this patent is extended or adjusted under 35 U.S.C. 154(b) by 575 days.

(21) Appl. No.: 12/196,078

(22) Filed: Aug. 21, 2008

(65) Prior Publication Data

US 2010/0049635 A1    Feb. 25, 2010

(51) Int. Cl.
    *G06Q 10/00* (2006.01)
(52) U.S. Cl. ............................ 705/28; 340/10.1; 700/214
(58) Field of Classification Search ................... 340/10.1
    See application file for complete search history.

(56) References Cited

U.S. PATENT DOCUMENTS

| | | |
|---|---|---|
| 2,965,242 A | 12/1960 | Grotke |
| 4,046,083 A | 9/1977 | Murdoch et al. |
| 4,866,255 A | 9/1989 | Sing |
| 4,919,282 A | 4/1990 | Duff et al. |
| 5,455,410 A | 10/1995 | Schneider |
| 5,500,651 A | 3/1996 | Schuermann |
| 5,513,459 A | 5/1996 | Schneider |
| 5,697,507 A | 12/1997 | Blass |
| 5,739,765 A | 4/1998 | Stanfield et al. |
| 6,352,163 B1 | 3/2002 | Barrett et al. |
| 6,371,311 B1 | 4/2002 | Barrett et al. |
| 6,393,339 B1 | 5/2002 | Yeadon |
| 6,464,142 B1 | 10/2002 | Denenberg et al. |
| 6,626,302 B2 | 9/2003 | Barrett et al. |
| 6,648,153 B2 | 11/2003 | Holmes |
| 6,874,684 B1 | 4/2005 | Denenberg et al. |
| 6,985,797 B2 | 1/2006 | Spano, Jr. et al. |
| 7,079,044 B1 | 7/2006 | Stanfield et al. |
| 7,093,755 B2 | 8/2006 | Jordan et al. |
| 7,123,989 B2 | 10/2006 | Pinney et al. |

(Continued)

OTHER PUBLICATIONS

"Pick-to-light directs productivity", Schwin, Gene F., Material Handling Engineering, Dec. 1993, vol. 48, iss. 12 , p. 43.*

*Primary Examiner* — M. Thein
(74) *Attorney, Agent, or Firm* — Dergosits & Noah LLP

(57) ABSTRACT

A system for easily locating goods stored in a storage area including a computer coupled with a radio frequency transmitter or transceivers and goods placed in containers that are coupled to hangers that each has distinct electronic addresses. The hangers each have a hook that allows the hangers to be stored on rails coupled to racks in a storage area. The identifications of the goods and the electronic addresses for the corresponding hangers are associated with each other and stored on a computer database. When a user wants to pick up goods stored in the containers, the user inputs the identification for the goods and the computer will cause the radio frequency transmitter to emit a data packet that includes a search address and illumination data. The hangers each compare the search address to the electronic address and if there is a match, the hanger illuminates the light according to the illumination data. The system notifies the user of the color and flash pattern and the goods can then be easily found by locating the hanger having the corresponding illumination.

14 Claims, 15 Drawing Sheets

U.S. PATENT DOCUMENTS

| | | |
|---|---|---|
| 7,194,333 B2 | 3/2007 | Shoenfeld |
| 7,301,470 B2 | 11/2007 | Stanfield et al. |
| 7,685,026 B1 * | 3/2010 | McGrady et al. ............... 705/28 |
| 7,751,932 B1 * | 7/2010 | Fedor et al. ................... 700/236 |
| 2001/0048057 A1 * | 12/2001 | Heisler et al. ............ 248/220.22 |
| 2006/0177291 A1 * | 8/2006 | Kienzl et al. ............. 414/331.15 |
| 2008/0017699 A1 * | 1/2008 | Jang .............................. 235/375 |
| 2008/0065264 A1 * | 3/2008 | Omura et al. .................. 700/231 |
| 2008/0116274 A1 * | 5/2008 | Aldridge ....................... 235/440 |
| 2008/0191842 A1 * | 8/2008 | Spenik et al. ................. 340/10.1 |
| 2009/0167500 A1 * | 7/2009 | Braun et al. ................. 340/10.1 |
| 2009/0173745 A1 * | 7/2009 | Parrish ............................. 221/2 |
| 2010/0198401 A1 * | 8/2010 | Waugh et al. ................. 700/237 |

* cited by examiner

PRODUCT STORAGE AND RETRIEVAL SYSTEM

BACKGROUND

An inventory of goods is frequently stored in a storage area. The distribution of the goods is monitored and controlled by an inventory worker. When an order is placed for the goods, a pick list is produced and the inventory worker obtains the required quantities of each of product on the pick list. The ordered goods can then be placed in a temporary storage area until the order is picked up. Because many orders can be placed at the same time, the filled orders must also be identified and organized so they can be easily located and given to the proper recipient. When the order is picked up, order information or identification information is given to the inventory worker who locates the filled order and gives the order to the recipient.

When the goods are controlled, it may be necessary to store the goods in a secure area. For example, a pharmacy may store many different drugs in an area that is only accessible to authorized employees such as pharmacists. A prescription from a doctor may be required to place and fill the order for these drugs. When an order is placed, a pharmacist will place the specified quantity of drugs into a container and then place the container in a storage area with the name of the patient marked on the container. When the patient picks up the prescription drugs, the pharmacist will compare the patient's identification with the patient's name on the prescription before delivering the medication(s) to the patient.

Various systems have been developed to assist users in locating the ordered goods stored in the inventory area. Goods can be stored in an alpha numeric order so that the user can quickly identify the location of a product by its name or number. For example, library books are typically stored by an associated code that is marked on the edge of the book.

A problem with existing systems is that they are inefficient since the user must manually locate the products in the inventory area which are typically stored in a numeric or alphabetical order. There is also a problem of locating the filled orders that have been placed in the temporary storage area. Since these tasks are performed manually, the location of goods and filled orders can require sorting through many items before the correct goods and filled orders can be located. It can be very difficult to pick out goods and filled orders with 100% accuracy. What is needed is a system that allows users to more easily locate goods in an inventory storage area or find filled orders within a temporary storage area.

SUMMARY OF THE INVENTION

The present invention is directed towards an apparatus and method for storing and locating goods and filled orders in a storage area. The storage apparatus can include one or more racks that are used to support a plurality of hangers which are each coupled to a storage container. Each hanger has a radio frequency receiver having a unique address and an indicator light. In an embodiment, the light can include one or more light emitting diodes which can each be different colors, such as red, green and blue. By simultaneously illuminating a combination of these lights at different intensities, the combination of these lights can produce various different colors. In the preferred embodiment, the inventive system is coupled to a computer network that includes a plurality of computers and the inventive system can be controlled by one or more of the networked computers which may be running proprietary software.

One or more of a specific product is placed in the container. The product and the hanger address are associated with each other and recorded on a computer database that is networked to one or more client computers. The containers can be various different structures including: bags, boxes, envelopes, etc. In order to help identify the products within the container, the container may be made from a translucent or transparent material. The container may have a closure, cover, latch or other device which allows the contents of the bag to be accessed and prevents the goods from accidentally falling out of the container. In some situations, the products cannot be placed in the containers. Instead of storing the goods in the container, a place card indicating the location of the goods may be placed in the container so the user can locate the desired goods. For example, if the goods are too large to fit in the container, the place card may indicate the larger storage location for the goods. If the goods require refrigeration, the place card may indicate that the goods are being stored in a refrigerated storage area. If the goods are controlled substances, the place card may indicate that these goods are stored in a locked area and additional security measures may be required to access the goods. If the goods are special prescription drugs that require a pharmacist to fill the prescription only when the patient arrives, the place card may indicate these requirements and provide the prescription filling instructions. The place card can provide various other location and instructional information for the goods.

When a recipient wishes to pick up the ordered goods, identification information for the ordered goods is input into a client computer. The computer searches the database to determine the address of the hanger associated with the goods. Once the address is found, the client computer instructs a radio frequency transmitter to emit a data packet that includes the address associated with the goods and is transmitted to the storage area where the hangers are kept. All of the hangers in the storage area receive the packet and compare the address to the assigned hanger address. In one embodiment, the hanger having a matching address responds by illuminating an indicator light (possibly a multi-colored light emitting diode) built into the hanger. All other hangers that are not the correct address will not react to the address signal and will continue to monitor for new incoming address packets. The computer operator will be informed about the color light on the hanger associated with the matching address and then the operator can easily locate the corresponding illuminated hanger and provide the contents of the container to the recipient of the goods.

The inventive system can have various special features that enhance the functionality of the invention. The inventive system utilizes radio frequency transmitters and receivers that utilize electrical power. The electrical power can be provided by batteries and/or electrical current from a standard alternating current electrical power supply or a combination of both. In an embodiment, a rail used to suspend the hangers may provide electrical power to the hanger. The hangers may also include rechargeable batteries that are charged while the hangers are on the rail. The hangers each include a hook that supports the container on a rail coupled to the rack. The lower surface of the hook may include two electrical contacts and the rail can include corresponding electrical strips that are coupled to an electrical power supply. When the hangers are placed on the rail, the electrical contacts physically contact the electrical strips which provide electrical power to the hangers.

In an embodiment, the electrical contacts attached to the hangers are metal pins that extend down from the bottom of the hook section. The pins can be coupled to springs that allow pins to move relative to the hook section. The pins remain in electrical contact with the rail even when the hanger is not perfectly aligned with the rail. The conductive strips can be mounted on the upper surface of the rail within grooves that extend along the length of the rail. The hangers of the inventive system can slide along the length of the rail while maintaining electrical contact with the electrical strips.

While the hanger is placed on the rail, the electrical contact provides power to the electrical components of the hanger. In the preferred embodiment, the electrical power is low voltage direct current which minimizes the possibility of electrocution. Thus, the electrical components may be damaged if the polarity of the pins and conductive strips is reversed. The rail may be designed so that it is impossible to reverse the polarity of the power by reversing the connections of the pins to the conductive strips. When the hanger is removed from the rail, the electrical components of the hanger are powered by a rechargeable power supply such as an in internal battery. The internal power supply allows the hanger to continue to operate by illuminating the lights when the radio frequency signal with the corresponding address is received. The power supply may provide enough power for the internal components to operate for one or more hours before recharging is required.

In another embodiment, the hanger may utilize a micro-capacitor as a rechargeable power supply rather than a battery. In this embodiment, the parallel plates of the capacitor may be oppositely charged by the direct current provided by the positive and negative polarity strips of the rail. When the hanger is removed from the electrical power, the electrical charge of the micro-capacitor is used to power the electrical components of the hanger for a limited period of time.

In other embodiments, the hangers may receive electrical power from the storage rails through an inductive charging mechanism rather than the direct contact conductive charging mechanism described above. The induction charging mechanism may use induction coils to create alternating electromagnetic fields from within the rail. Each of the hangers may include an induction coil that is placed in the hook portion of the hangers that takes power from the electromagnetic field and converts it back into electrical current to charge the internal rechargeable power supply. In order for the hangers to obtain power from the rail, the two induction coils must be in close proximity to each other. In order to align the coils, the rail may have many coils centered across the width and equally spaced along the length of the rail. In order to align the hangers with the coils, the rail may have alignment mechanisms such as a recessed portion that allows the hook portion of the hangers to be placed directly over the coils. The recessed area may correspond to the width of the hook portion of the hanger. Alternatively, the primary inductive coil in the rail can extend along the length of the rail. The charging coil of the hanger may be within the tab section and the hangers may be able to slide along the length of the rail while still allowing for inductive power transfer to the hanger. A benefit of inductive charging is that there are no exposed electrically conductive surfaces. The coils are preferably concealed within the housing of the hangers. This configuration minimizes the possibility of foreign objects preventing the conductive components from contacting each other.

In an embodiment, many different products or orders may be retrieved simultaneously and several different hangers can be illuminated simultaneously. In order to distinguish the illuminated hangers for the different products or orders, each of the hangers can be illuminated in a different color and/or flash pattern. When the computer transmits a packet with a hanger address, additional light instructions can also be included in the packet. The light instructions can specify an illumination color and a flash pattern. When the hangers receive the address signals, they will first determine if the assigned address matches the received address and if the addresses match, the hanger will read the illumination instructions. The illumination instructions can instruct the hangers to illuminate the indicator lights in distinct colors or blinking patterns. For example, two addresses may be transmitted from the client computer to the hangers. A first hanger can be a match for the first address and the corresponding illumination instructions may be a fast pulsing red light. A second hanger can be a match for the second address and the corresponding illumination instructions can be a slow pulsing green light so that the worker can distinguish the first and second orders.

The workers will be informed of the illumination associated with each of the goods or orders and can look for a hanger having a specific color and illumination display pattern associated with each part or each order. The user can find the matched hangers based upon the light display and remove the hanger from the rack. When the hanger is removed from the rack, the indicator light may continue to be illuminated by the internal power supply. The user can then bring the container to the recipient and the computer may record the removal of goods from the storage area. The computer may also record the receipt of goods by the recipient using an input device such as a biometric finger print reader or any other type of identification mechanism.

In an embodiment, an additional check can be performed to insure that the proper goods are being delivered to the recipient. The hangers may have a secondary identification device such as a bar code, serial number code, radio frequency identification tag, magnetic coding, etc. The secondary code associated with the hanger can be read by an input device to verify that the secondary code corresponds with the order. These secondary identifications can be associated with the goods or filled orders prior to storing the hangers on the racks. When the container is retrieved from the storage area, the address of the hanger can be compared to the goods and the secondary identification can also be checked. A mismatch between the secondary identification can indicate an error in the goods or order. Additional safety mechanisms may also be incorporated. For example, the container may have a locking device which can only be opened when the secondary identification is confirmed by the hanger. In this embodiment, the locking device can be an electronic mechanism which disengages when the secondary identification is received in an RF signal. If the address and secondary identification are verified, the contents of the container can be delivered to the recipient.

Once the transaction is complete, and the goods delivered the hanger and container can be reused. The container may be restocked with the same parts and the hanger can be placed on the rack so that the hanger address can remain associated with the same parts. Alternatively, a new order can be placed in the container and the goods or order can be associated with the hanger and recorded on the computer before being stored on the rack.

While the invention has been described with reference to delivery of pharmaceuticals, the inventive system can be used for various different storage and distribution applications. The products can be stored by product type wherein each of the containers holds a single product. When a user needs several different products, a different hanger must be obtained for each product. The system can be configured to illuminate all of the hangers needed to fill an order with the same light color(s) and illumination pattern. This allows the user to locate and collect all hangers that are needed. When the quantity of product runs low, the product placed in the container can be replenished and the hanger replaced on the rack. Since the product remains the same for the hanger, the hanger can always be associated with the same product.

Alternatively, each container can store a group of different products that have been picked in order to fill an order for a recipient. This embodiment may be particularly suitable for pharmacies where patients require specific quantities of several different medications. In this embodiment, a patient may receive a prescription for several medications. The prescriptions can be forwarded to the pharmacist who gathers the prescribed drugs and places them in a single container coupled to a hanger. The hanger and coupled container are associated with the patient on the computer system and stored on a rack in the storage area. When the patient arrives at the pharmacy to pick up the prescription, the pharmacist can input identification for the patient and the computer will transmit the radio frequency signal to the hangers. The hanger coupled to the container holding the patient's medication will be illuminated and easily identified so the medication can be easily retrieved and given to the patient.

DETAILED DESCRIPTION

Figure 1:
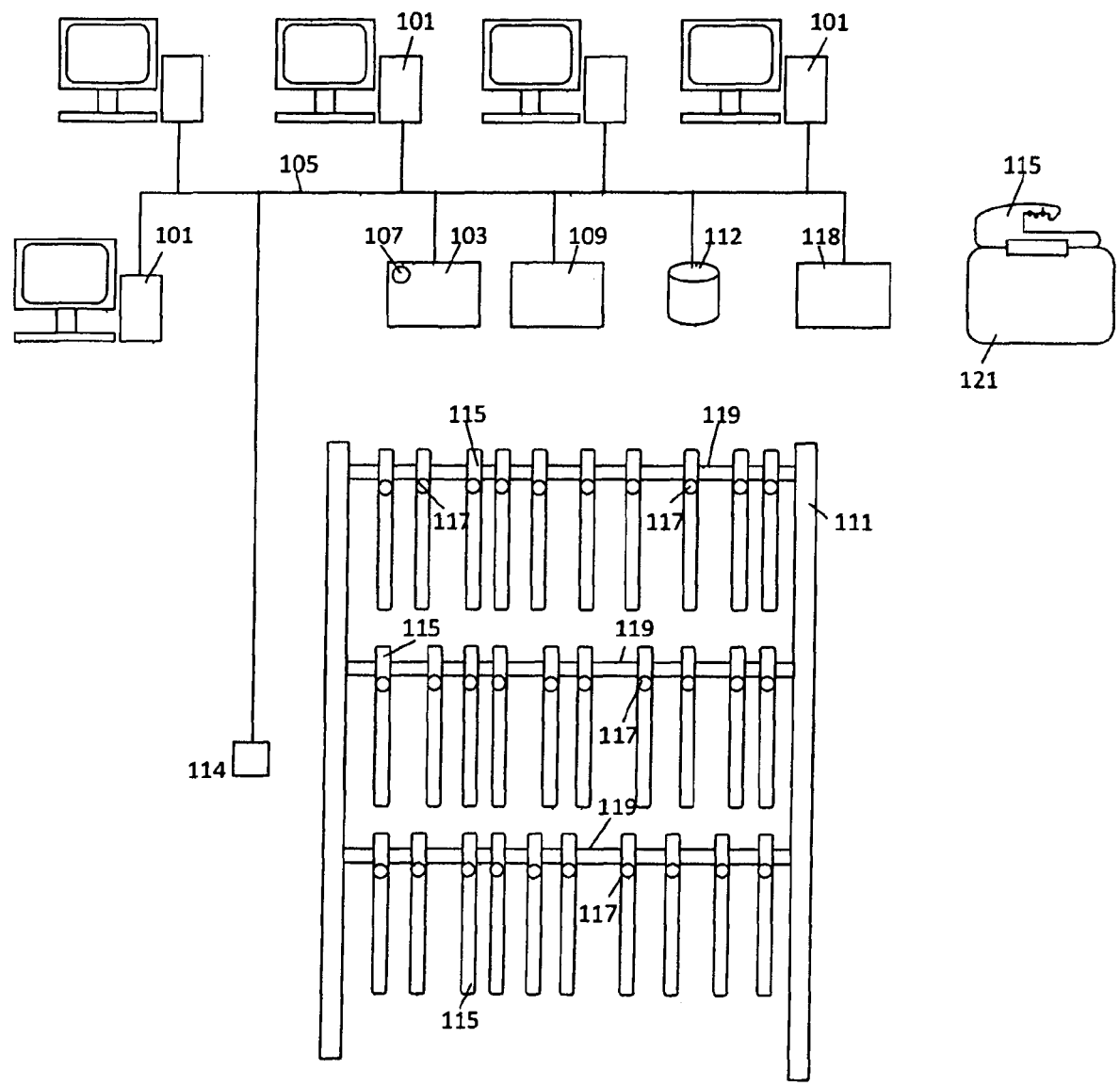
FIG. 1 is an illustration of the storage system components.

The present invention is directed towards an apparatus and system for storing and locating products within a storage area. With reference to FIG. 1, in an embodiment the inventive system includes several separate components. The inventive system can be used with a computer network having a plurality of client computers 101. The clients 101 are coupled to one or more radio frequency (RF) transmitters or transceivers 103. One or more of the clients 101 can be an administrative computer that controls the operation of the inventive system. The RF transmitters or transceivers 103 may be coupled to one or more status lights 107 which can indicate that the transceiver 103 is operating properly. For example, a green light may be illuminated when the transceiver 103 is connected to the network. A red light may indicate that the transceiver is powered and functional. The red light may blink when there is an error in the system. A yellow light may indicate that the wireless receiver is enabled. A storage rack 111 includes a plurality of substantially horizontal rails 119 which provide a storage area for a plurality of hangers 115. Each hanger 115 includes: a hook, a container, an RF receiver and one or more indicator lights 117.

Goods are placed into the containers 121 coupled to each hanger 115. The addresses of the hangers 115 and the quantities and identifications of the goods placed in the associated containers 121 are input and stored in the computer 101 memory in a database. In an embodiment, the addresses are part of a code that is attached to each of the hangers and can be read with a code reader 109. The description of goods can be a name of the goods, a description or a code representing the goods. Codes representing goods can be standardized within an industry and include: Stock Keeping Units (SKUs), Universal Product Code (UPC), National Drug Code (NDC), European Article Number (EAN), Global Trade Item Number (GTIN) and Australian Product Number (APN). The goods and the addresses of the hangers are associated with each other and this association is stored on a database 112 that is accessible by the client computers 101.

In an embodiment, the computer can be coupled to various input devices. While the identification of the hangers and goods can be entered manually through a keyboard it is also possible to enter data in various different ways. A secondary identification can be useful in providing additional verification information to prevent accidental or erroneous transactions. In an embodiment, the electronic input mechanism can provide an electronic verification of a digitized identifier. For example, the system may include an input device 118 which can be used to read information such as RFID tags or bar codes attached to the hangers. For example, goods that have a UPC code will also have a bar code and the scanner 118 can be a bar code reader. An operator of the system can scan the bar code with the input device 118 that communicates with the computer 101 through a wired or a wireless connection. Other possible input devices 118 can include optical scanners, RFID tag readers, magnetic strip readers and other data input devices. By scanning or reading an address for the hangers and an identification associated with the goods, data input into the computer can be simplified. The quantities of goods placed in each container can also be entered through the input devices described or manually through a numeric key pad.

The hangers 115 are then placed in the storage area. In the preferred embodiment, the hangers 115 and containers 121 are thin structures that can be placed adjacent to each other on a storage rail for space efficiency. The containers 121 can be various different types of devices that securely hold goods. Suitable containers 121 including: bags, boxes, envelopes, tubes, baskets, bins, etc. The containers preferably include closure mechanisms such as: slots, flaps, lids, covers, tabs, etc. The closure mechanisms preferably utilize a coupling device to secure the closure mechanism after the goods have been placed in the container 121. The closure devices can include: latches, hooks, buttons, snaps, Velcro, zippers and other suitable fasteners. The hanger can also be releasably coupled to the container so that the containers can be changed or replaced if necessary. The connection between the container 121 and hanger 115 can include: bolts, screws, clips, hooks, clamps, Velcro, zippers and other fasteners.

In some situations, the goods cannot be placed in the containers 121 coupled to the hangers 115. Instead of storing the goods in the container 121, a place card indicating the storage location of the goods may be placed in the container 121. When the hanger 115 is located, the user will find the place card and be informed of the location of the desired goods. The user can then go to the specified location to obtain the required goods. The place card may also include additional instructions that must be completed to obtain the goods. There are various reasons why the goods should not be placed in the containers 121 attached to the hangers 115. For example, if the goods are too large to fit in the container 121, the place card may indicate the larger storage location. If the goods require refrigeration, the place card for the goods may indicate that the goods are being stored in a refrigerated storage area. If the goods are controlled substances, the place card may indicate that these goods are stored in a locked area. Additional security measures may be required in order for the recipient to receive the controlled goods. If the goods are special prescription drugs that require pharmacists to fill the prescription only when the patient arrives, the place card may have these instructions. The patient may be required to bring the instructions to the pharmacist who will then fill the prescription.

The client computers 101 may also be coupled to a radio frequency verification receiver 114 that is placed by the hangers 115 and used to check the transmissions from the transmitter 107. When the transmitter 107 emits the data packets, the verification receiver 114 detects the signals to determine if the hangers 115 were also likely to receive the data packets. If the verification receiver 114 does not detect the data packets there may be a failure within the system. The client computer 101 may retransmit the radio frequency packet and if the signals are repeatedly not detected by the verification receiver 114, the system can be reset and retested. Continued failure may cause the system to issue an error message to the operator.

Figure 2:
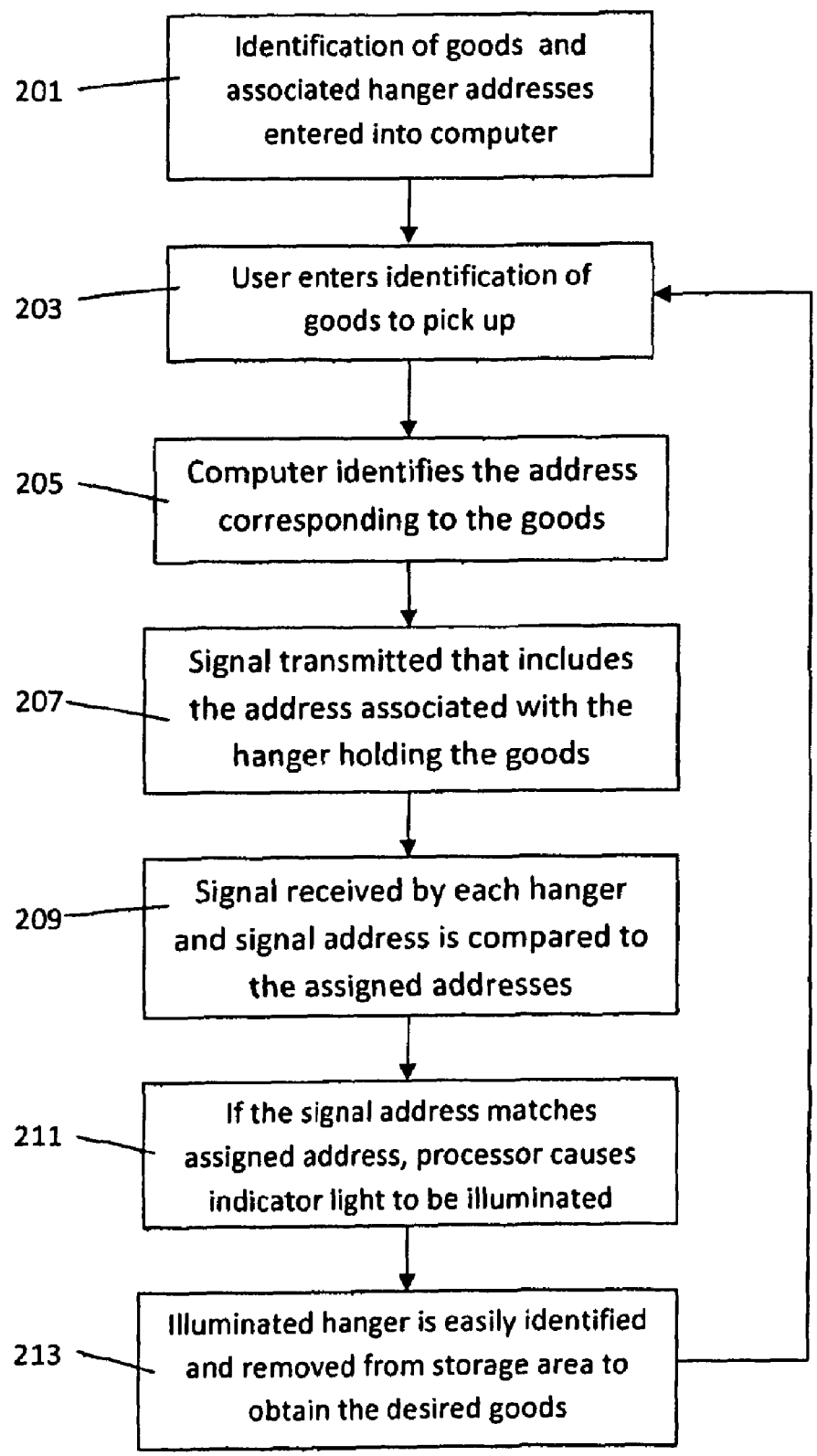
FIG. 2 is a flow chart for locating goods.

With reference to FIG. 2, a flow chart of the basic process used to locate goods is illustrated. The goods are identified and placed in the containers coupled to the hangers and the identification of goods and the associated hanger addresses are entered into the computer 201. When someone needs to obtain the goods, the identification information for the goods is entered into the computer 203. The quantity of goods may also be entered. The computer identifies the address corresponding to the goods through the database 205 and transmits a signal through the RF transmitter such as a data packet that includes the address associated with the hanger holding the goods 207. The RF signal data packet is received by the receivers in each of the hangers in the storage area and each hanger may perform a data check to determine if the packet has been corrupted. If the data is corrupt, the incoming packet is discarded. If the data packet is not corrupt, the hanger compares the address in the packet to their assigned addresses 209. If there is a match, the hanger instructs the indicator light to be illuminated 211. The user can then easily find the illuminated hanger to obtain the desired goods 213 in the storage area.

In an embodiment, the inventive system can be used in installations where multiple goods stored in several different hangers are being picked simultaneously. In order to enable multiple hangers to be picked at one time, the illuminated indicator lights for each hanger must be a distinct signal to avoid mixing goods or orders. In this embodiment, the computer can transmit an illumination signal with the address signal through the RF transmitter to the hangers. The illumination signal can include a color and/or illumination pattern data. When the hanger receives the corresponding address signal, it can respond by illuminating the indicator light in the color and flash pattern corresponding to the illumination data.

Figure 3:
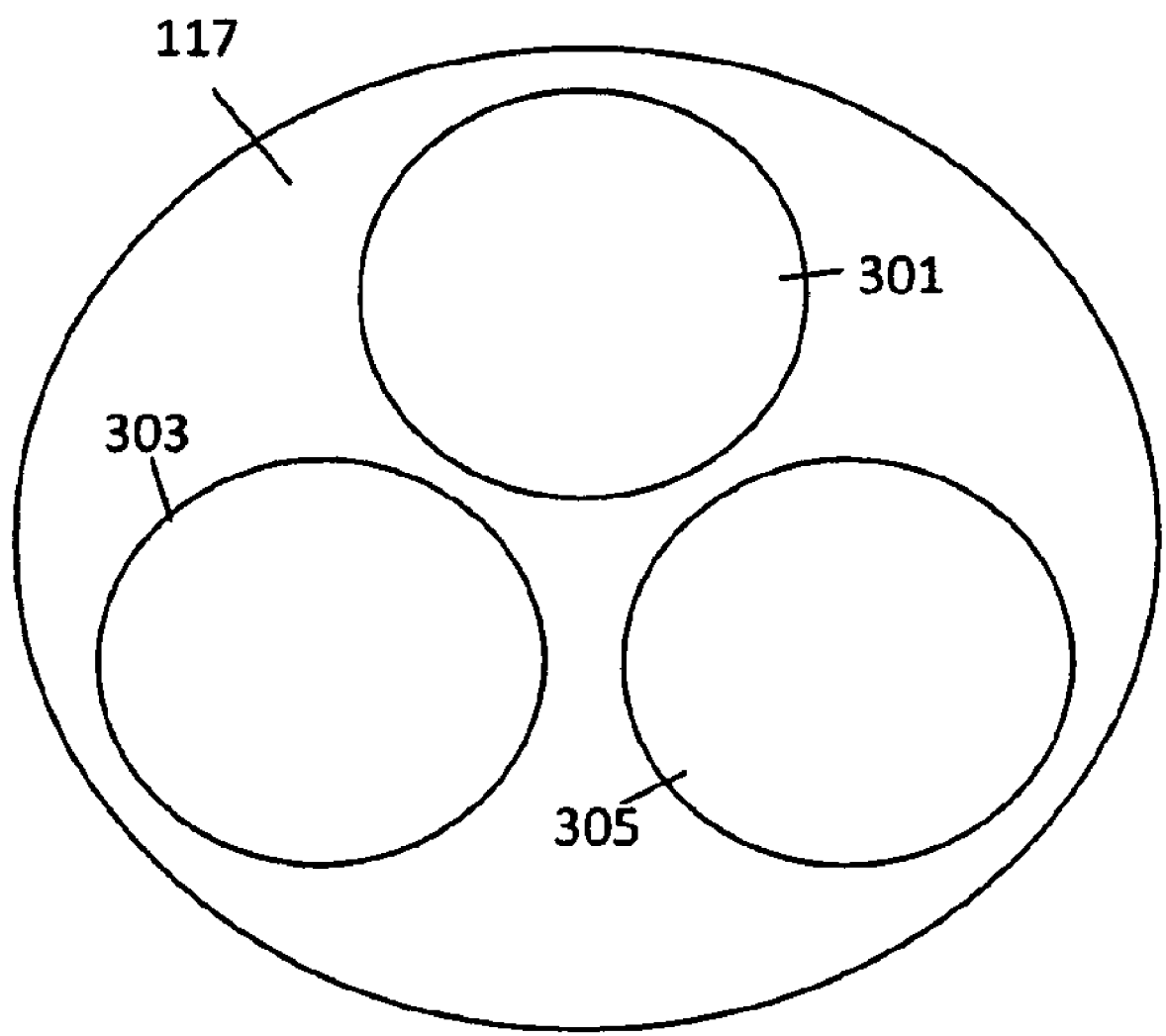
FIG. 3 is a view of a multi-colored LED.

With reference to FIG. 3, in order to produce a light color, the indicator light 117 may include separate red 301, green 303 and blue 305 (RGB) lights that are placed in close proximity of each other to form a single light output. By controlling the output of each of the primary color lights, many different colors can be emitted by the indicator light 117. With reference to table 1 below, the distinct colors created by illuminating one or more of the red 301, green 303 and blue 305 lights are specified. In addition to the colors listed in table 1, additional color variations can be created by changing the output intensities for the red 301, green 303 and blue 305 (RGB) lights. Thus, if multiple hangers receive corresponding address signals, each can produce different illumination outputs so the hangers are not mixed.

TABLE 1

| Color | Red | Green | Blue |
|---|---|---|---|
| Blue | Off | Off | On |
| Green | Off | On | Off |
| Cyan | Off | On | On |
| Red | On | Off | Off |
| Magenta | On | Off | On |
| Yellow | On | On | Off |
| White | On | On | On |

Figure 4:
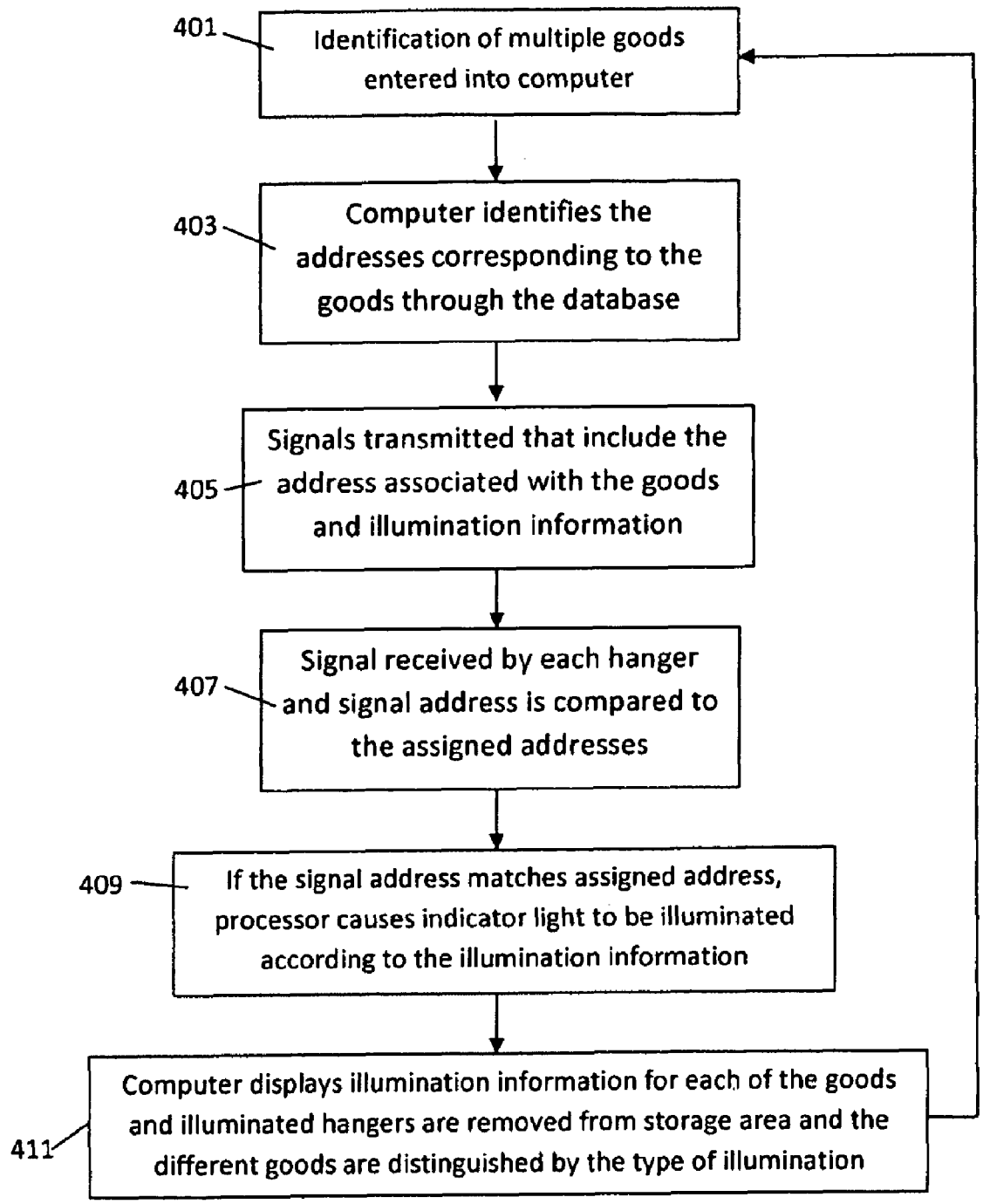
FIG. 4 is a flow chart for storing and retrieving goods using different illumination information.

When multiple hangers are being picked up at the same time, the different colors can be used to distinguish the hangers which can each contain different goods. With reference to FIG. 4, when a user needs to find the goods or hangers, the user inputs identification information for each of the goods or hangers into the computer 401. The client computer uses the identification information to identify the hanger addresses associated with the goods through a database 403. The client computer then controls the RF transmitter to emit multiple RF signals that can be data packets. Each data packet can include a different address and a distinct illumination instruction 405. The client computer will also inform the worker which color is associated with each good or order being located. For example, if a first patient needs pain medication and a second patient needs indigestion medication, the client computer may transmit a first address for aspirin with a red illumination signal and a second address for antacids with a green illumination signal. The hangers will receive each of the data packets and compare the addresses received to the assigned address 407. If the address in the data packet is an exact match, the hanger will illuminate the indicator light in the accordance with the illumination instructions 409. The client computer will inform the worker that the hanger with the red light is aspirin and the hanger with the green light is antacids so that the worker will be able to identify and distinguish the hangers 411. Using this feature, multiple medications can be easily identified obtained from the storage area and given to the proper patients.

Another method for differentiating the hangers based upon illumination patterns is through variable pulses in the illumination. With reference to Table 2 below, various illumination patterns are described based upon a repeating sequence of 16 time slots which each represent 125 milliseconds. The first goods can be in a hanger that emits a sequence of evenly timed pulsed illuminations each lasting about 1 second on and 1 second off which is represented by Flash Rate 1. The second goods can be in a hanger that emits a faster series of pulses that last 0.25 seconds (two time slots) on and only 0.25 second off represented by Flash Rate 3. The computer can indicate the illumination pattern so the hangers can be identified and distinguished based upon the illumination patterns. The system may also have specific flash patterns to indicate errors or normal operation. For example, a low battery or power supply may be indicated by a pattern of three 0.125 second flashes on followed by an off duration of 1.25 seconds. The illumination pattern indicating charging can be represented by 0.875 seconds on followed by 0.5 seconds off and 0.25 seconds on. While some flash patterns are listed in table 2, many other flash patterns are possible. In other embodiments, the illumination instruction can include a combination of different colors and pulse patterns.

TABLE 2

| | Repeating Sequence of Time Slot | | | | | | | | | | | | | | | |
|---|---|---|---|---|---|---|---|---|---|---|---|---|---|---|---|---|
| Flash Rate | 1 | 2 | 3 | 4 | 5 | 6 | 7 | 8 | 9 | 10 | 11 | 12 | 13 | 14 | 15 | 16 |
| Off | off | off | off | off | off | off | off | off | off | off | off | off | off | off | off | off |
| On | on | on | on | on | on | on | on | on | on | on | on | on | on | on | on | on |
| Flash Rate 1 | on | on | on | on | on | on | on | off | off | off | off | off | off | off | off | off |
| Flash Rate 2 | on | off | on | off | on | off | on | off | on | off | on | off | on | off | on | off |
| Flash Rate 3 | on | on | off | off | on | on | off | off | on | on | off | off | on | on | off | off |
| Flash Rate 4 | on | off | off | off | off | off | off | off | off | off | off | off | off | off | off | off |
| Low Battery | on | off | on | off | on | off | off | off | off | off | off | off | off | off | off | off |
| Charging | on | on | on | on | on | on | on | off | off | off | off | off | on | on | off | off |

By informing the user of the illumination color and flash pattern, the hanger containing the desired goods can be located and removed from the storage area. The container attached to the hanger can be open and the goods can be removed so that the order can be checked for accuracy. The delivery of goods is recorded on the computer so that the identity and quantity of goods can be accounted for. Additional information such as time of delivery and recipient identification can also be recorded. After the desired goods are removed, the hanger can be refilled with the same or different goods and revised goods information can be associated with the hanger address and input into the computer database. Alternatively, the disassociation of the goods from the hanger address can be input in the database and the hanger may remain empty until it is reused.

Figure 5:
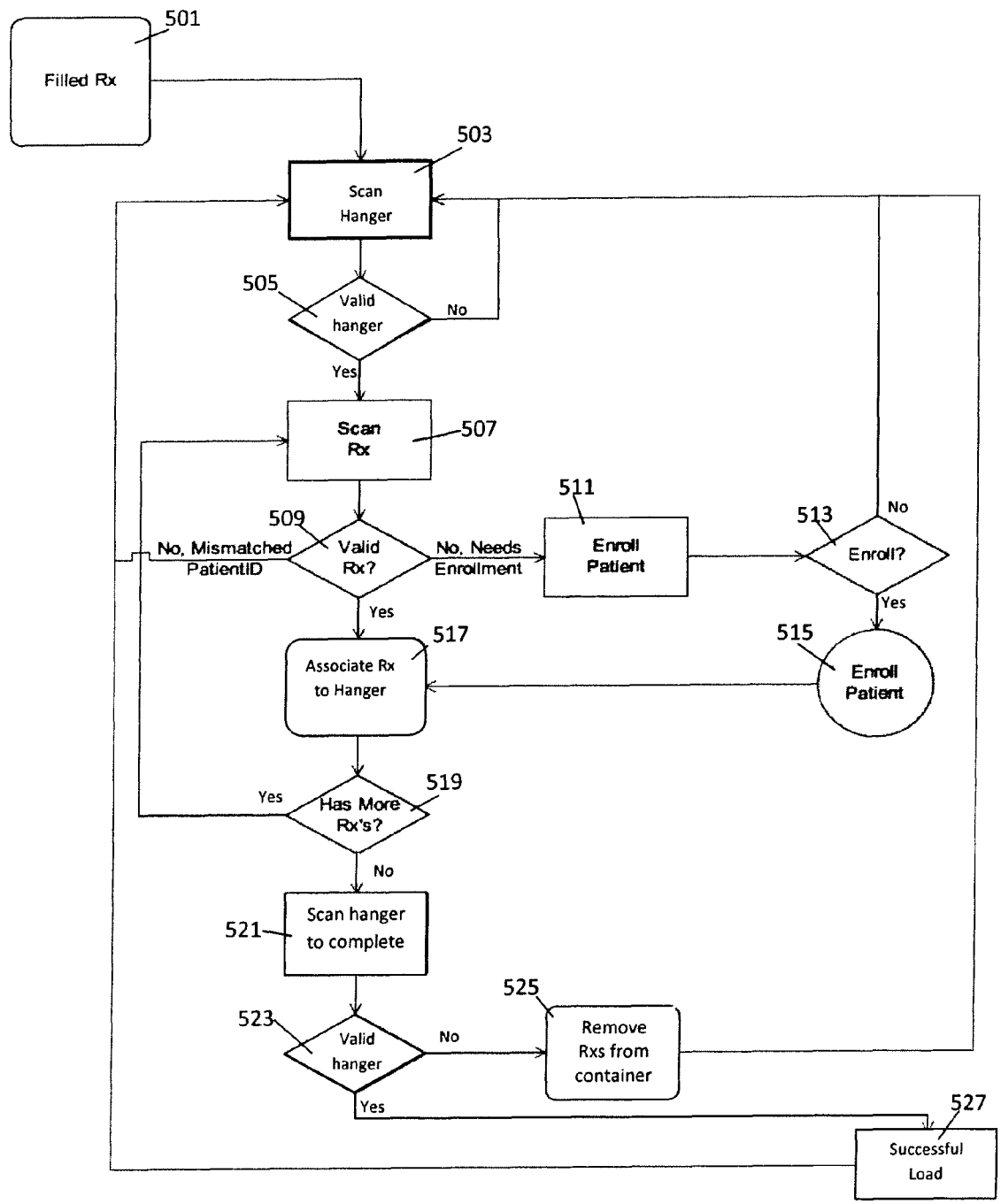
FIG. 5 is a flow chart for storing and retrieving prescriptions for patients.

While the general operation of the inventive system has been described above, it is also possible to use the system for specific applications. The inventive system may be particularly suited for use with the distribution of prescriptions through pharmacies. In these embodiments, additional safeguards are required to prevent errors and unauthorized use since this can result in serious health risks. With reference to FIG. 5, a flowchart of an exemplary use of the inventive system is illustrated. A prescription is first filled by the pharmacist 501 by gathering the required medications 501. The pharmacist then obtains a hanger and scans the hanger to obtain the identification or address 503. The identification of the hanger is checked by the computer to verify that it is valid 505. If the hanger is not valid, the pharmacist may need a new hanger and the scanning step is repeated 503. If the hanger is valid, the computer checks the validity of the prescription 509. The system can be configured to check for various prescription errors. For example, if the prescription has been previously filled and stored in another hanger the system will detect this error by identifying the other hanger containing the prescription. The system may also cross reference the patient's medical records to verify that the prescription is not in conflict with the medical history and issue a warning or stop the process if there is a conflict. The system will also compare the patient identification to the system records. If the patient ID is mismatched, system identifies the error and stops the prescription filling process until the problem is resolved. If the prescription is valid, the system computer associates the prescription with the hanger address 517 and stores this association on the database.

The system will also check the patient identification to determine if the patient is not enrolled in the patient database. If the patient is not enrolled, the system can go through an enrollment process for the patient 511. The patient is given the option of enrolling 513. If the patient does not enroll the process is stopped and the prescription is not filled. If the patient enrolls 515, the system associates the prescription with the hanger 517. During the validation process, the system may record the number of prescriptions stored in each container, the date and time that the prescriptions were placed in the containers, the pharmacist performing the prescription filling or any other information that may be useful.

After the prescription has been validated and placed in the container coupled to the hanger and the prescription has been associated with the hanger address and stored this information on the computer database, the system will check if there are additional prescriptions 519. If there are additional prescriptions, the system will repeat the validation process. If there are no other prescriptions, the hangers can be scanned 521 to recheck the validity 523. If the hanger is invalid, the prescriptions are removed from the container 525 and the prescriptions are refilled with a valid hanger. If the hanger is valid, the prescription filling is completed and the hanger is placed in the storage area 527.

Figure 6:
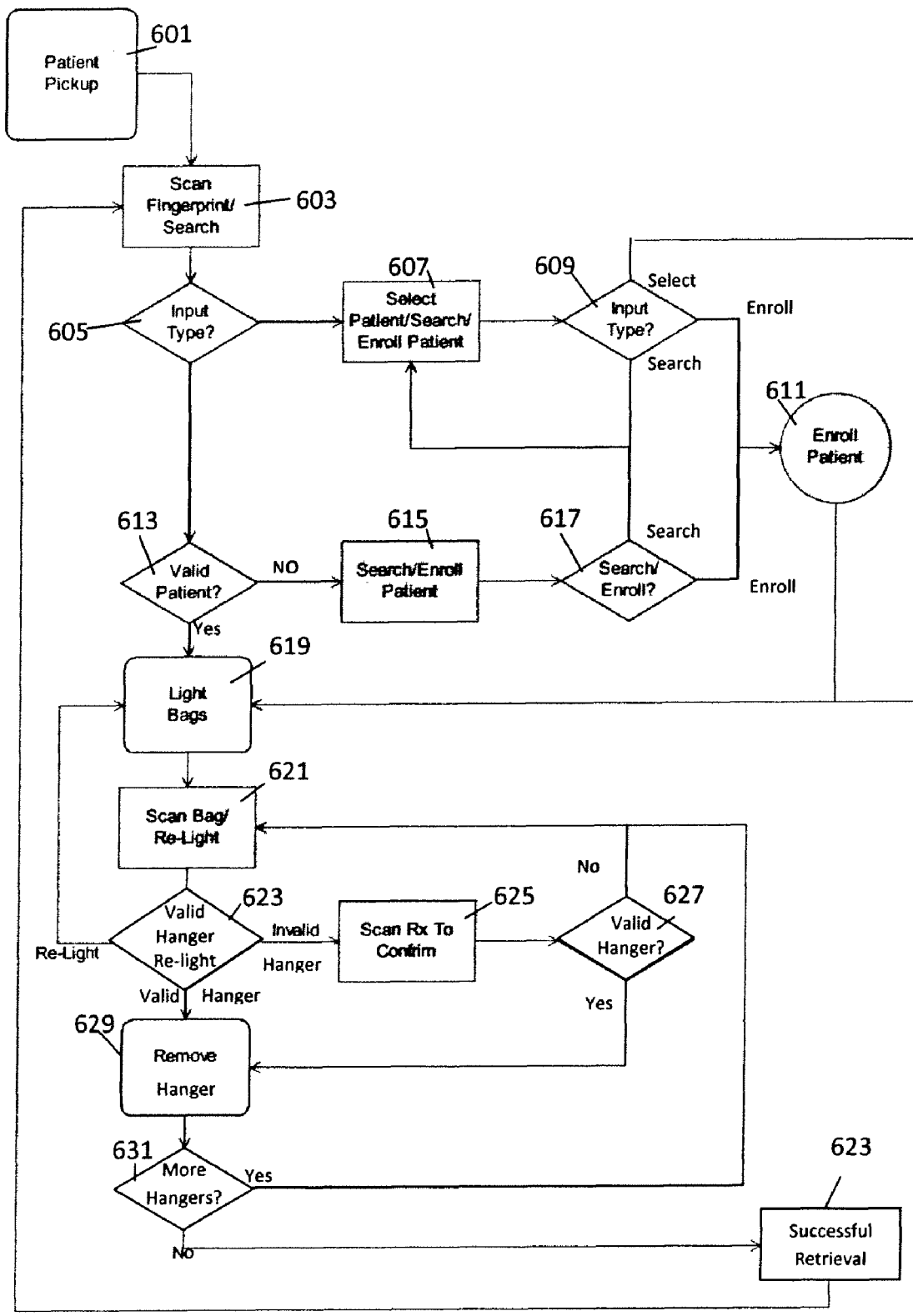
FIG. 6 is a flow chart for retrieving prescriptions for patients.

When the patient arrives to pick up a prescription, the system may perform specific procedures to prevent distribution errors. With reference to FIG. 6, a flowchart of an exemplary prescription retrieval process is illustrated. The patient arrives to pick up the prescription 601. The identification of the patient can be verified 603 by providing various types of identification information. In an embodiment, the system may utilize a biometric device such as a finger print scanner to identify the patient. Alternatively, the patient can input identification information that can be searched. The type of identification information input into the system is determined 605 and the processing of the identification information will vary depending upon the type of information input. If the identification is a biometric scan, the patient identification may be verified by this information alone. Alternatively or if the finger print scan was not recognized, other identification data can be input and verified by the system 607. For example, the identification information may include: patient ID number, first name, last name, date of birth, phone number and gender. The system may provide a function list of select, search or enroll if the patient is not yet in the system 609. In some cases, multiple patients may have the same name or date of birth and a list of matching patients may be listed and the operator can select the proper patient. If the patient is not enrolled, the system can perform the enrollment for the patient 611.

If the patient inputs identification data, the system will then check the validity of the patient 613. If the patient identification is not valid, the system will ask if the user wishes to search the patient database or enroll the patient 615. The user can respond by instructing the system to search the patient database or enroll the patient 617. If the user selects the search function the system will search for the patient as described above and if the enrollment is selected, the system will proceed to the enrollment process 611.

Once the patient identification has been verified, the system will transmit the RF packet with the corresponding hanger address for the prescription. The indicator light will illuminate on the hanger with the matching address that contains the prescription for the patient 619. The user can remove the hanger from the storage area and scan the hanger 621 with an input device such as a bar code reader to verify the proper hanger has been removed. The system will check the scanned hanger data and either verify the hanger identity or indicate that an error has been made 623. If an error has been made, the system will retransmit the address signal to the hangers and the user can locate and remove the proper hanger. Alternatively, if there is a malfunction with the hanger, the prescription medications can be removed and checked to verify that they are for the patient 625 before being given to the patient. The hanger can also recheck to determine if it is valid 627. If the hanger is invalid, it can be removed from the system. If the hanger is valid, the hanger is removed 629 and the contents of the container are given to the patient. The system will then inform the pharmacist if there are any more prescriptions store in other hangers for the patient 631. If the patent has more prescriptions, the system will repeat the described process. If the patient does not have any more prescriptions, the pick up process will be complete 623. After the prescriptions have been retrieved, the patient may have to sign a confirmation of receipt which can be recorded with the transaction files. The signature may be a digital signature with a stylus on a tablet or any other signature means. The hangers are unassociated from the patient and stored until they are reused and associated with other patients.

Figure 7:
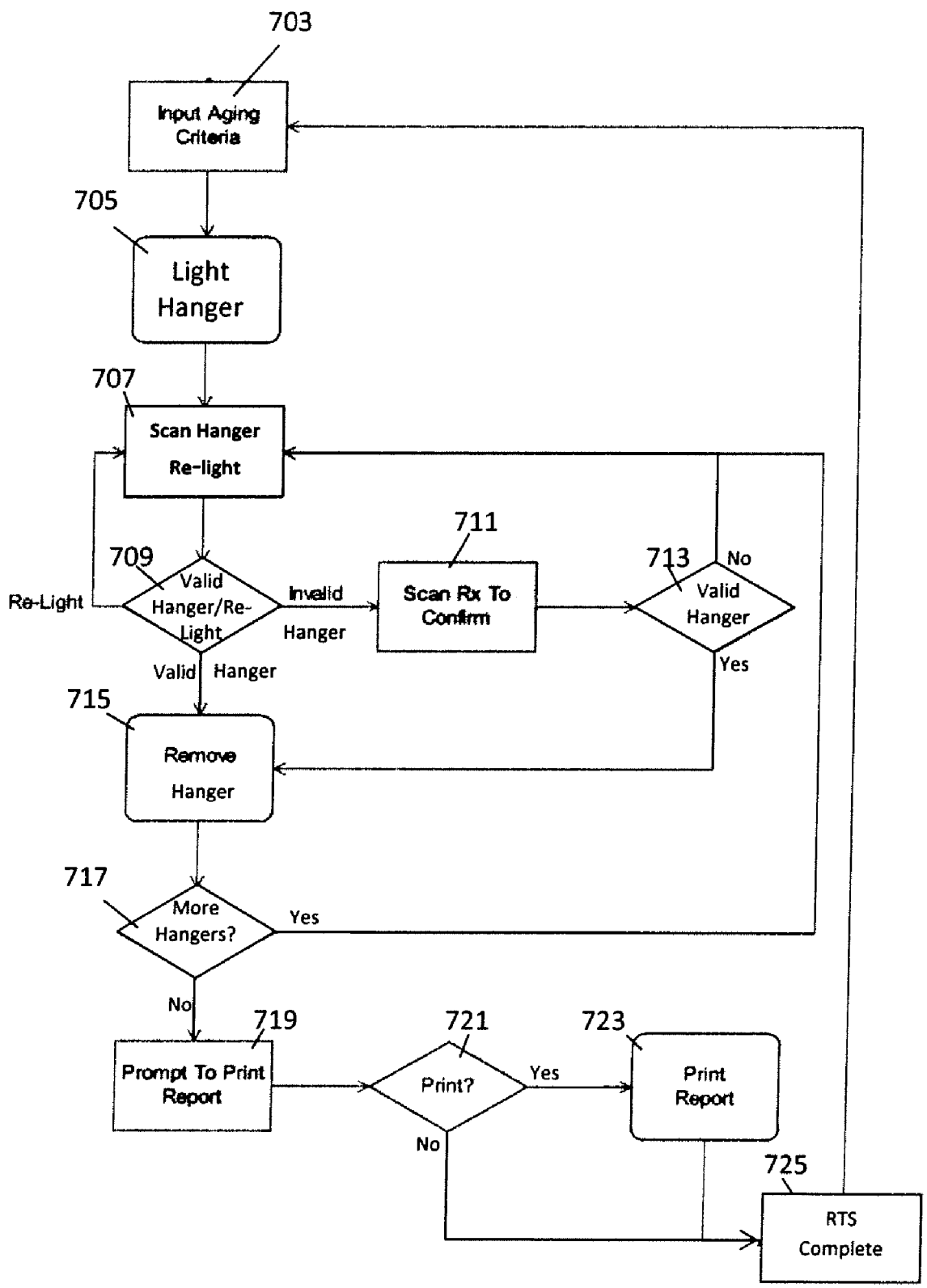
FIG. 7 is a flow chart for restocking goods that have not been picked up.

The inventive system can also perform additional tasks and store additional information about the goods placed in the containers. This information can be used by the system for various purposes. For example, the goods placed in the container may have been part of an order picked from an inventory area for customer pick up. If the customer decided not to pick up the goods, the system may be configured to have the goods restocked after a predetermined period of time. For example with reference to FIG. 7, a flow chart showing a process by which the inventive system can be used to restock goods if the customer has not picked up within a predetermined time period after the order is placed. The return to stock removal processing can set at regular time intervals such as everyday or when the system is not being used or in low usage. The input age removal criteria are input into the system 703. The criteria can be a restocking time that is variable depending upon the types of goods being stored. For example, food will have to be removed from storage much faster than medication or goods that do not have a shelf life. The system can compare the age removal criteria to the information on the goods stored in each hanger.

When the system detects that a restocking time period has elapsed, the client computer transmits RF packets to the hanger addresses having goods that need to be restocked. These hangers receive the packet and respond by illuminating their indicator lights 705. The worker can then remove the illuminated hangers and scan them 707. If the hanger is valid 709, the hanger and associated container are removed and the contents can be restocked. If the bag is invalid, the prescription can be removed from the container and scanned to confirm that they should be restocked 711. The system may also recheck the validity of the hanger 713. If the hanger is invalid and not operating correctly, it can be removed from service and repaired or replaced. If the hanger is valid, it can be reused. The system will then determine if there are additional hangers with goods that need to be restocked 717. If there are more goods in the order, the system relights the hangers with goods to return to stock so they can be removed. If there are no more goods in the order, the system may ask the user if a print out report is desired 719 for the hangers and goods that were removed from the storage area. The worker can then respond to the print prompt 721. If a print out is requested, the system will print the report 723 and alternatively, if the print out is not required the return to stock routine is complete 725.

Figure 8:
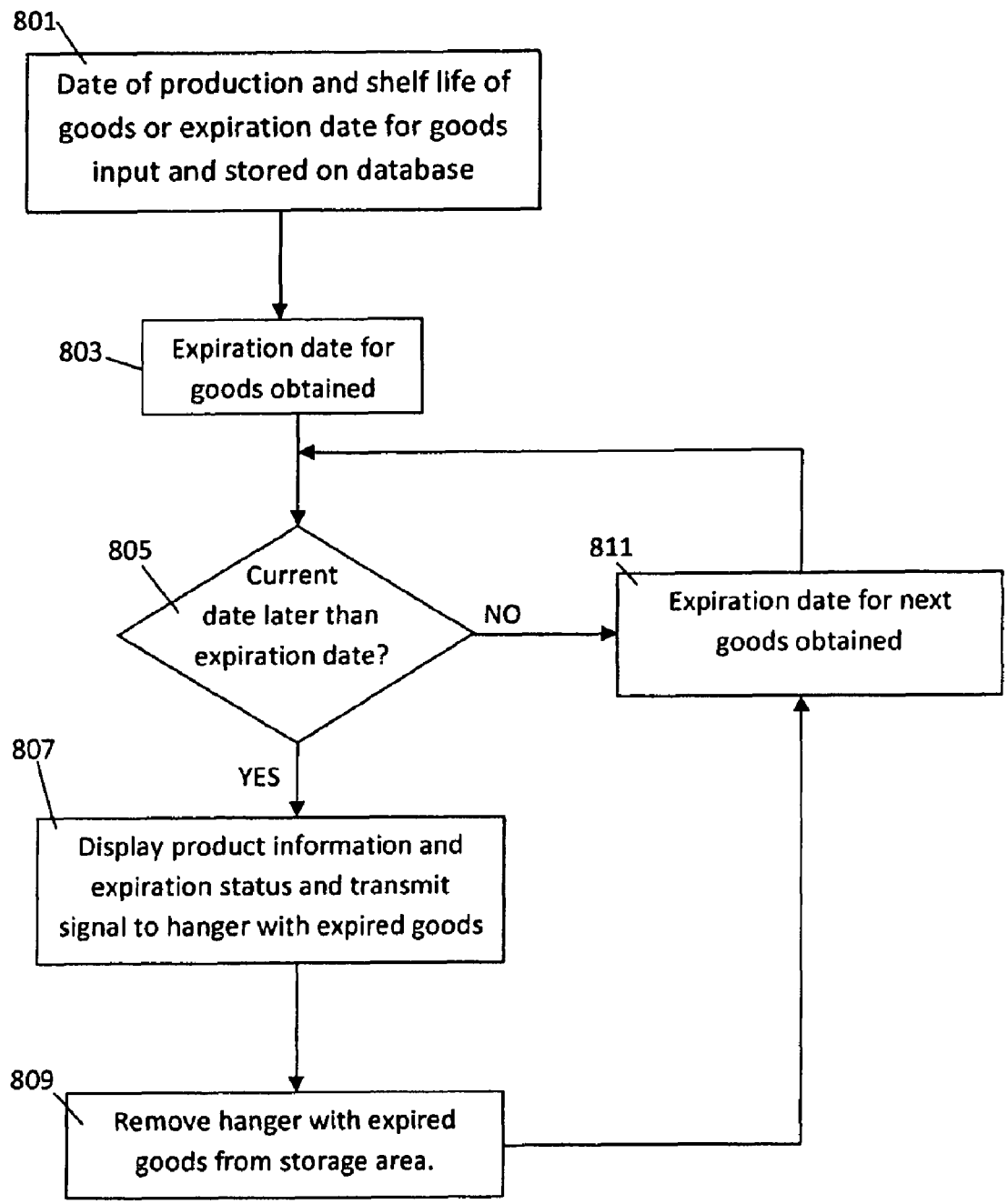
FIG. 8 is a flow chart for removing expired goods.

The inventive system can also be used to perform other tasks. For example, the inventive system can be used to prevent the distribution of expired goods is illustrated in the flowchart shown in FIG. 8. Many goods such as food or medication have a limited shelf life. In order to avoid distribution, the date of production and shelf life can be stored on the computer 801. The computer can then calculate the expiration date and compare the current date to the expiration date. The computer may continuously check the status of each good having an expiration date 803. If the expiration date or a predetermine time prior to the expiration date has passed 805, the computer can inform the user that the certain goods have expired and need to be removed. The inventive system can transmit a signal that includes the hanger address associated with the expired goods and provide a visual display message on a screen that the goods are expired 807. The worker will be alerted to this problem and remove the illuminated hangers that contain the expired goods 809. In an embodiment, the expired goods can have a designated illumination color or pattern. For example, a solid red light may indicate that the goods coupled to the hanger are expired. The worker can then replace goods with fresh goods and input the revised information for the new goods into the computer database. If the expiration date has not expired, the system will proceed to the next goods having an expiration date 811. In the preferred embodiment, the system will check all goods having an expiration date on a daily basis.

In the preferred embodiment, the inventive system utilizes special hardware components that allow the system to function as designed. In the preferred embodiment, the hangers include electrical components that are powered by an external power source that is coupled to the storage rails. In order to perform the power transfer, special components are utilized that include electrical contacts that allow power to be transferred from the external power source through the rods in the storage area to each of the hangers.

Figure 9:
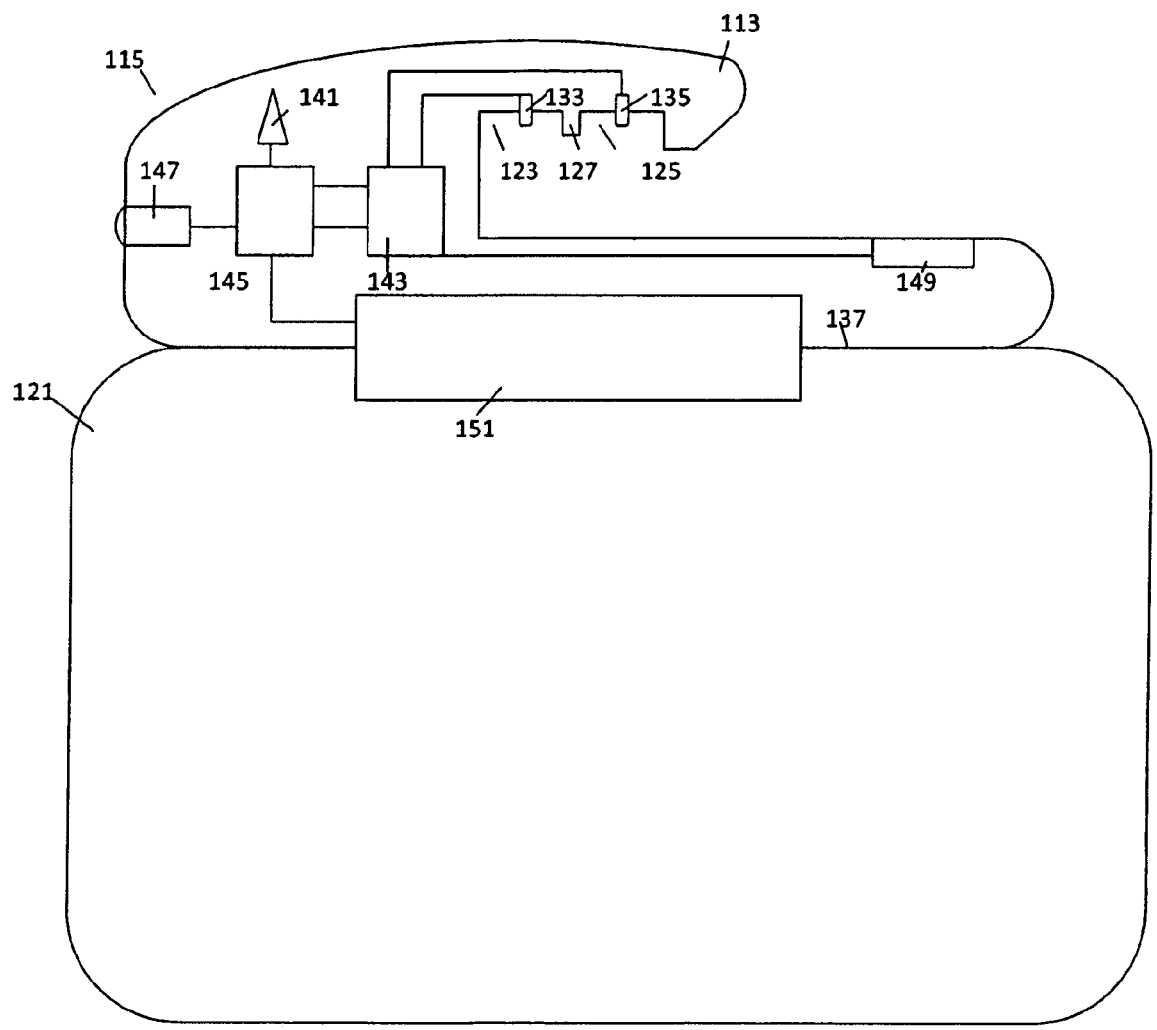
FIG. 9 is a cross sectional view of an embodiment of a hanger.

With reference to FIG. 9, a cross sectional view of an embodiment of the hanger 115 is illustrated. In this embodiment, the hanger 115 includes a hook 113 portion that has a first recessed area 123 that is separated from a second recessed area 125 by a tab 127. The lower portion of the hanger 115 includes a connector 137 that is coupled to a container 121. The RF receiver 141 is coupled to an internal power supply 143, a microprocessor 145 and an indicator light 147. The electrical components are housed within the external shell of the hanger 115 which protects the components. The indicator light 147 can be partially exposed through a hole in the hanger 115 so that a user can see if the indicator light 147 is illuminated. The hanger 115 may also include a serial connector 149 that can be coupled to a computer for maintenance and debugging. In an embodiment, the power supply 143 can be a rechargeable battery or in an alternative embodiment the power supply 143 can be a microcapacitor.

The receiver 141 receives the RF data packets that includes an address and forwards this information to the microprocessor 145 which has a predetermined address. The address can be a made up of four bytes of data represented by any number between 0.0.0.0 and 255.255.255.255. If the address in the packet is an exact match for the predetermined address, the microprocessor 145 will emit a match signal which causes the indicator light 147 to be illuminated. If the RF signal address is not an exact match, the microprocessor 145 will ignore the RF signal and the indicator light 147 is not illuminated. In other embodiments, the system will receive additional information which can be used for specific actions. For example, the hanger may include a locking mechanism 151 for the container which prevents unauthorized access to the contents. The locking mechanism 151 may be an electrical device that is actuated by the microprocessor 145. When the hanger is brought to a station, the hanger may require a confirmation signal to unlock the locking mechanism 151. In this embodiment, the operator may have to input a confirmation code into the computer. The confirmation code may only be used by authorized system users. The computer will then emit an RF data packet that includes the confirmation code. The hanger will receive the confirmation code and the microprocessor 145 will compare it to a predetermined code. If the confirmation code is a match, the microprocessor 145 will unlatch the locking mechanism 151. If the confirmation code is not a match, the latch will remain locked and the contents of the container may not be accessible until the proper code is received.

If the power supply is a battery, the electrical components of the hanger 115 can be powered by a power supply 143 that is a battery alone. However, this may require the power supply 143 to be high powered or recharged regularly in order to prevent failure of the system. Alternatively, the electrical components can be powered from an external source. For example, the rods in the storage area can provide electrical power to the electrical components while the hanger 115 is stored on the rail. This electrical power can also be used to recharge the power supply 143 when the hanger 115 is placed on the rail. In order to provide electrical power, the hanger 115 can have electrical contacts. In an embodiment, the hanger 115 can have a first electrical contact 133 that extends into the first recessed area 123 and a second electrical contact 135 that extends into the second recessed area 125. The tab 127 is an elongated straight structure that engages a groove in the rail and aligns the first electrical contact 133 and the second electrical contact 135 with electrical strips in the rail and improves the electrical contact. The first and second electrical contacts 133, 135 are used to power the RF receiver 141, microprocessor 145 and indicator light 147 and recharge the power supply 143.

In the preferred embodiment, the power supply 143 is a rechargeable battery. When the hanger 115 is placed on the rail, the internal rechargeable batter is charged by electrical power from the rail. When the hanger 115 is removed from the rail, the rechargeable battery provides electrical power to the electrical components of the hanger 115 by discharging a stored electrical charge. The rechargeable batteries come in many different designs using different chemicals. Commonly used types of rechargeable batteries include: lead and sulfuric acid, rechargeable alkaline battery (alkaline), nickel cadmium (NiCad), nickel metal hydride (NiMH), lithium ion (Li-ion), and lithium ion polymer (Li-ion polymer).

In an alternative embodiment, the power supply can be a micro-capacitor. The micro-capacitor is an electrical device that can store energy in the electric field between a pair of conductors called plates. The capacitor stores energy by charging the plates by applying an electric charge of equal magnitude, but opposite polarity, on each plate. When the capacitor is removed from the power supply, the plates can discharge their stored electrical power. Thus, when the hanger 115 is placed on the rail, the micro-capacitor power supply can be charged and when the hanger 115 is removed from the rail, the capacitor can discharged the stored electrical energy and provide power to the electrical components of the hanger 115.

Figure 10:
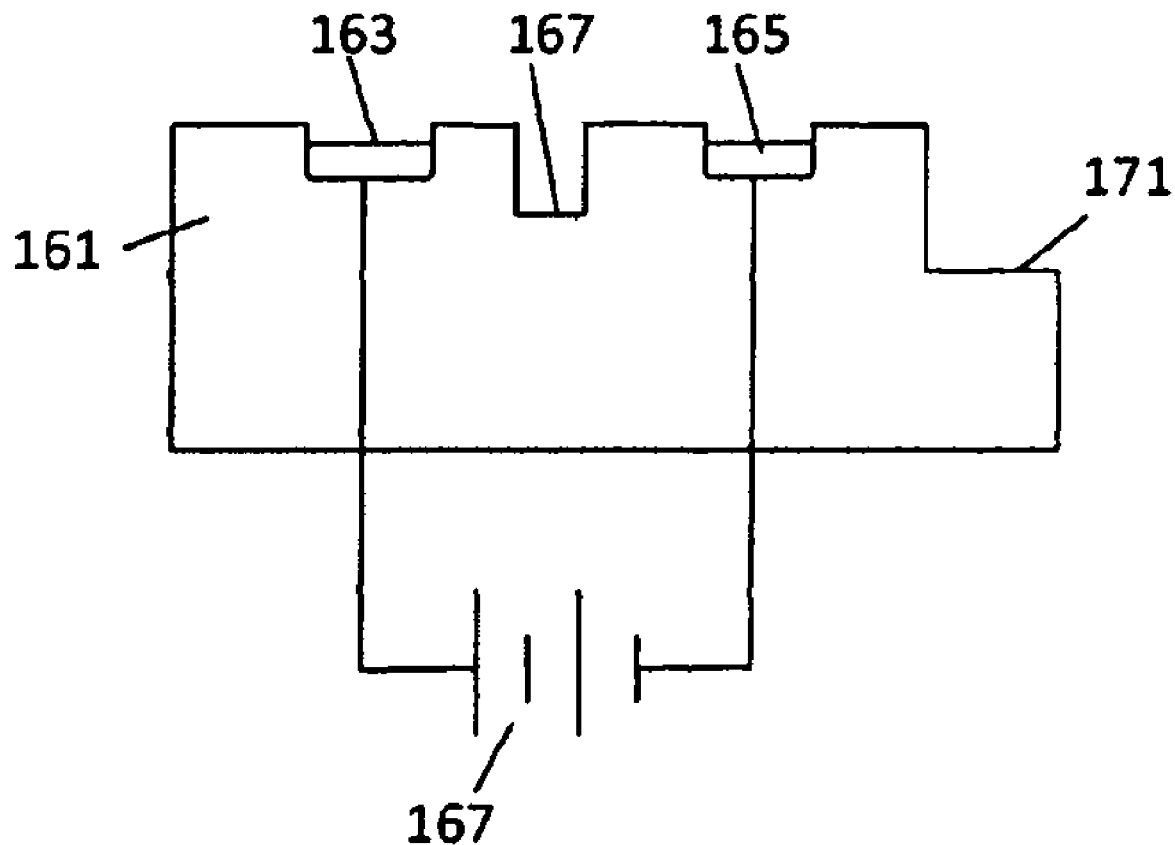
FIG. 10 is a cross sectional view of the storage shelf rail.

The electrical power is preferably a low voltage direct current, although in other embodiments an alternating current electrical power supply may also be used with electrical rectifier circuitry. With reference to FIG. 10, a cross section of a rail 161 for supporting the hangers is illustrated. The rail has two conductors 163, 165 that extend down the length so that the electrical contact will be maintained when the hanger is placed in any location along the length. Because the hangers are preferably setup for direct current, the negative power lead of the electrical power supply 167 can be coupled to one conductor 163 and the positive power lead can be coupled to the other conductor 165. A groove 167 is placed between the two conductors 163, 165 which is slightly wider than the tab of the hangers. The tab fits within the groove 167 and holds the hangers at a substantially perpendicular angle to the rail 161. This aligns the electrical contacts with the conductors 163, 165 and insures proper electrical contact between the hangers and the rail 161. The electrical power supply 167 will typically provide electricity to several rails 161 which can be wired in parallel or in series.

Since applying a reversed polarity will damage the electrical components, the rail 161 may have a mechanism that prevents the hanger from being placed on the rail 161 incorrectly. For example, the rail 161 may have a tab 171 that extends from the back side and runs along the length of the rail 161. Since the hook portion of the hanger is only open on one side, the tab 171 would prevent the electrical contacts from contacting the conductors 163, 165 unless the hook is in the proper orientation relative to the rail 161.

In order to properly utilize the inventive system, the power requirements must be determined and provided to the hangers. In an embodiment, each of the hangers may require 250 mA of current and 3.6 DC volts. Each hanger may be 1.5 inches wide so a 48 inch shelf rail will be able to hold a total of 32 hangers. If there are 5 shelf rails on each rack frame each having 32 hangers there will be 160 hangers on each rack frame. The total current required for each rack frame will be 160×250 mA=40 amps and the power required will be 3.6 volts×40 amps=144 watts. The power supply must have an output that is larger than the power drawn by the hangers. If the system is powered by a single power source, in order to provide a safety factor, the power supply may be 20% or more higher than the power requirements. Thus, a 230 watt, 3.6 volt power supply will provide more than enough power for this exemplary system. In the preferred embodiment, a power transformer and rectifier are used to provide power to the system. The transformer may convert 110 volt alternating current to 3.6 volts of direct current. In other embodiments, other voltages can be used. For example, the hangers may operate at 12 volts and the rails may be coupled to a 12 volt power supply.

In yet another embodiment, the hanger 116 may utilize an inductive electrical charging system. Inductive charging systems transfer AC power by magnetically coupling a primary winding on the supply side to a secondary winding coil in the hangers. Electrical current flows through the primary inductive coil producing a magnetic flux that induces an alternating current through the magnetic field and across the secondary inductive charging coil. The AC current is converted to DC for storage in the power supply.

Figure 11:
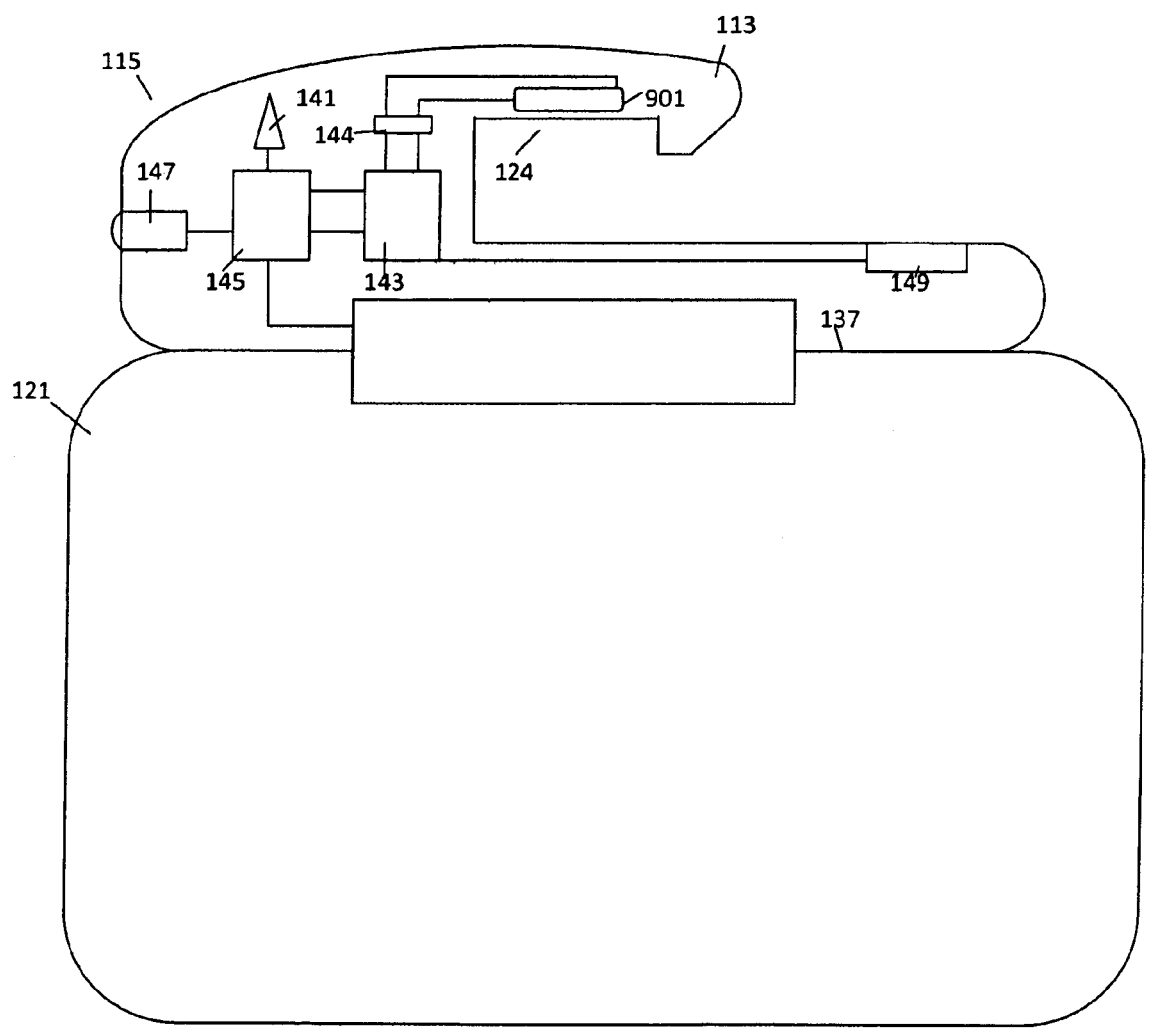
FIG. 11 is a cross sectional view of an embodiment of a hanger having an inductive coil.

FIG. 11 illustrates an embodiment of a hanger 116 having an inductive charging coil 901 is. Because the inductive charging system utilizes alternating current, the electrical output from the inductive charging coil 901 is also alternating current. In order to properly charge the power supply 143, the AC electrical power is passed through a rectifier 144 which converts the alternating current into direct current which can then be used to charge the power supply 143. In this embodiment, the hanger 116 may have a single recessed area 124. The hanger 116 can also includes all of the components described above with reference to FIG. 9.

Figure 12:
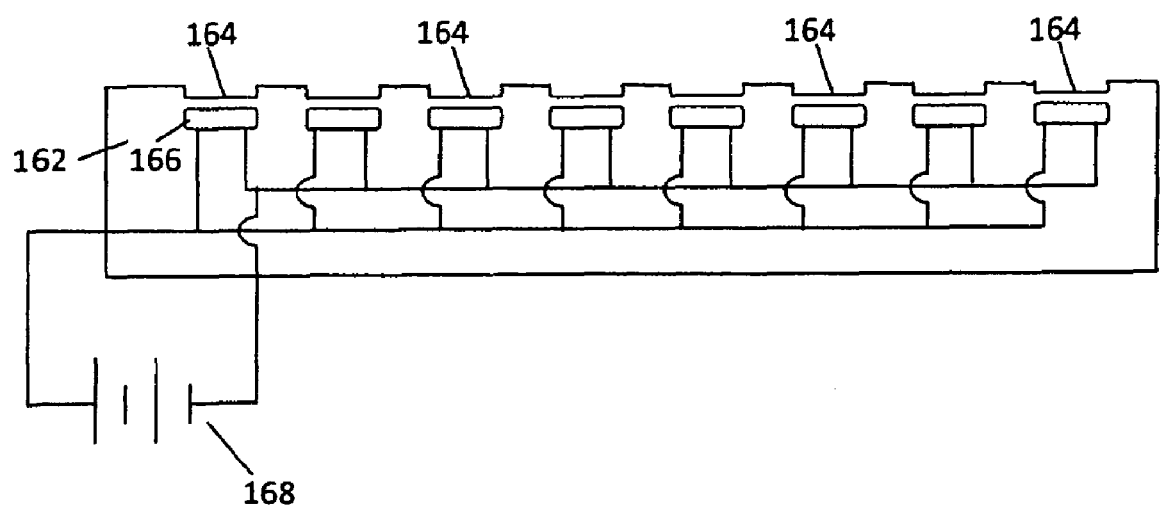
FIG. 12 is a view of the storage shelf rail having primary inductive coils.

With reference to FIG. 12, an embodiment of the rail 162 is illustrated having primary inductive coils 166 that are coupled to an alternating current power supply 168. In these embodiments, the hanger 116 may have a single recessed area 124 which is used to align the inductive charging coil 901 with one of the recessed areas 164 along the length of the rail 162. The width of the recessed areas 164 may correspond to the width of the hook portion of the hangers 116. By aligning the recessed areas 164 of the rail 162 with the recessed area of the hook portion of the hangers 116, the primary inductive coils 166 and the secondary inductive charging coils 901 can be aligned for inductive charging. In other embodiments various other mechanical systems can be used to align the primary and secondary coils 901. The alternating current from the alternating current power supply 168 flows through the inductive charging coil 901 producing a magnetic flux that is transferred to the inductive charging coil 901 of the hanger 166. The inductive charging coil 901 responds to the magnetic flux by producing an alternating current within the hanger 116. A rectifier 144 converts the alternating current into direct current which is used to charge the power supply 143. As discussed above, the power supply 143 provides electrical power to the electrical components of the hanger 116 when the hanger 116 is removed from the rail 162.

Figure 13:
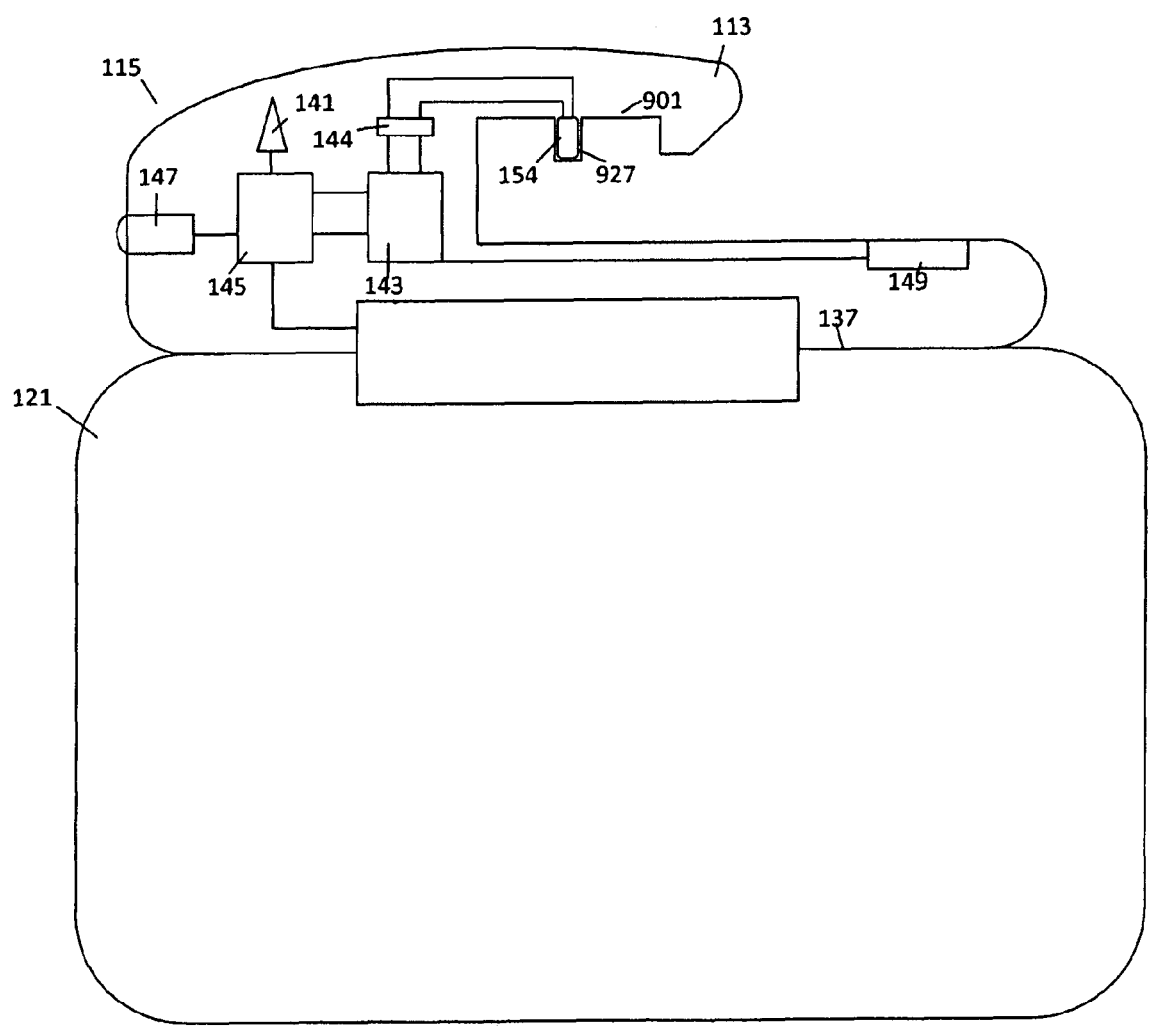
FIG. 13 is a cross sectional view of an embodiment of a hanger having an inductive coil.
Figure 14:
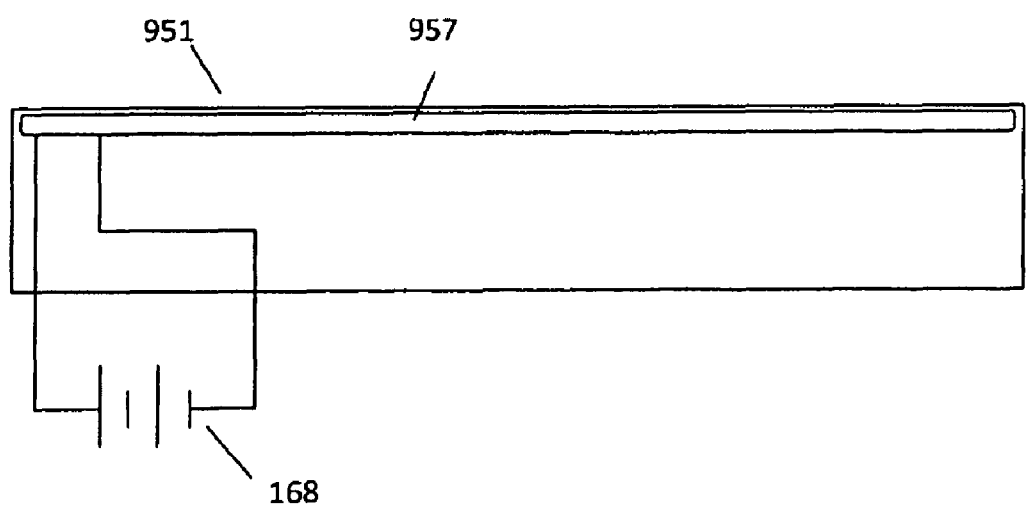
FIG. 14 is a view of the storage shelf rail having primary inductive coils.

FIG. 13 illustrates another embodiment of the hanger 120 having an inductive charging coil 903 mounted within a tab 927. The inductive charging coil 903 can be aligned vertically so that it can receive magnetic energy from the sides of the tab 927. The other electrical components of the hanger 120 may be similar to the components described above with reference to FIGS. 9 and 11. FIG. 14 illustrates a side view of a rail 951 which has a primary inductive coil 957 that extends along the length of the rail 951. The primary inductive coil 903 is coupled to an AC power supply 168. When the hanger 120 is placed on the rail 951, the tab 927 fits within a groove (not shown) which is adjacent to the primary inductive coil 903. This positioning of the tab 927 within the groove places the inductive charging coil 903 of the hanger 120 in close proximity to the primary inductive coil 903. In this embodiment, the hangers 120 can be slid to any position along the length of the rail 951 and receive inductive power from the primary inductive coil 957.

For optimized performance, a specific configuration of the RF devices and the alignments of the antennas might be required. Because the hangers are aligned across the rail and the same surface faces outward for each hanger, the transmitter should be placed in a position substantially perpendicular to the rail so that all hangers will have line of sight position relative to the transmitter. In the preferred embodiment with reference to FIG. 13, a cross sectional view of an embodiment of the hanger 115 is illustrated. The antenna 171 is coupled to the microprocessor 145 and is aligned to optimally receive RF signals that are directed towards the edge of the hanger 115.

The hanger 115 may also include electrical shielding layers 175 that blocks RF signals from the sides of the hanger 115 and prevent cross talk between adjacent hangers. The shields 175 can include a metal layer that is placed along the sides of the hanger 115 but not the perimeter edge. This non-shielded area along the edge of the hanger 115 allows signals from the RF transmitter to be received without any interference. Since the antenna 171 will only receive signals from the unshielded edge, the antenna 171 can be a directional unit that can more easily detect RF signals from the unshielded edge.

Figure 15:
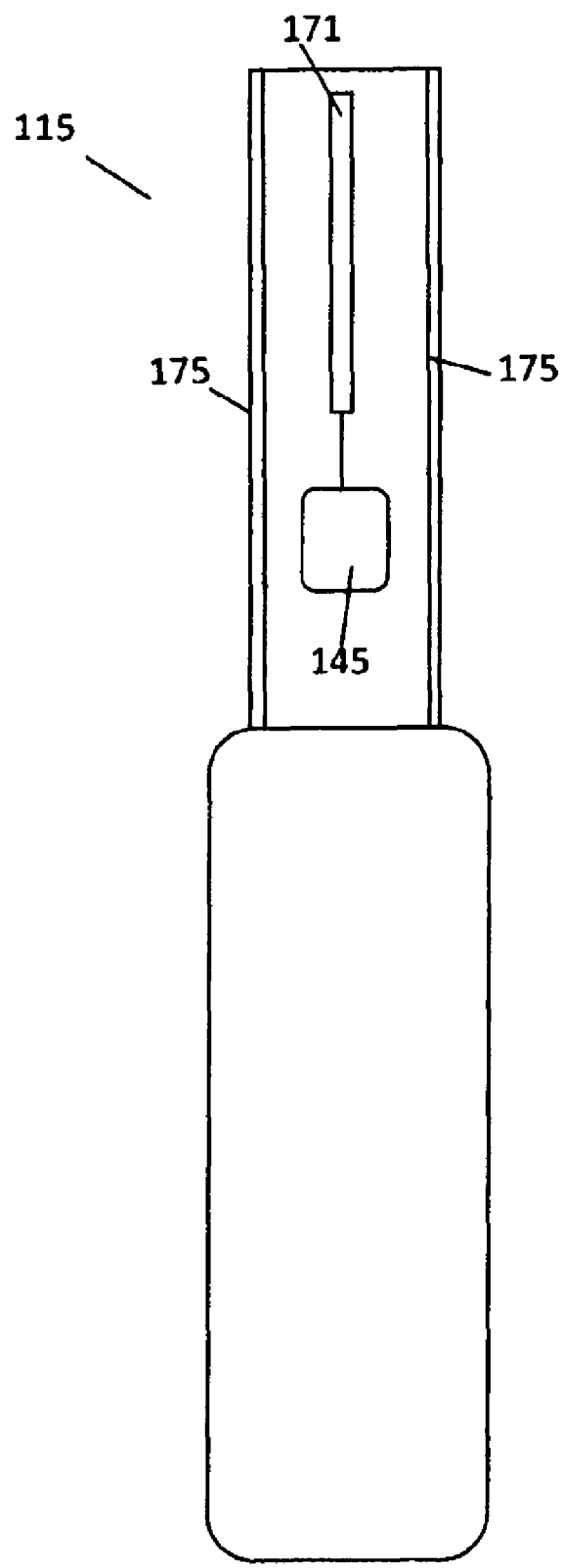
FIG. 15 is a view of an embodiment of a hanger having radio frequency shielding.

The inventive system has been described as a unidirectional communications system where signals are transmitted from the client computer through the RF transmitter to RF receivers in the hangers. In other embodiments, the RF communications devices coupled to the client computer and the hangers are transceivers which are capable of both receiving and transmitting RF signal data packets. In the transceiver embodiment, the system can be configured to provide feedback to the system. The shielding 175 illustrated in FIG. 15 can be particularly important when the hanger 115 includes an internal transceiver.

A benefit of this configuration is the ability to obtain confirmation of the communications and detect errors in the system. Without the transceivers, a client computer may attempt to transmit an address within a data packet through the transmitter and the hanger with the matching address may not respond by illuminating the indicator light. The system may automatically retransmit the data packet in anticipation of some data transmission failures. If the transmission signals are not properly processed, there is no indication of where or if the signal was lost, it can be very difficult to diagnose and correct the problem with a transmittal only system.

The transceiver embodiment can provide improvements to the inventive system because a transceiver in the hanger will provide a confirmation of the receipt of communications between the system and the hanger. This allows the processing of the goods to be tracked by the system. For example, a computer coupled to a network may instruct the transmitter to emit a data packet that includes an address for a hanger. The data packet is transmitted and the hangers compare the address with the assigned address. The hanger having the matching address will then emit a confirmation signal with the corresponding address receives the data packet. The system can monitor the transmission and receipt of RF signals and based upon this information, the system can determine the status of each RF data packet. This information can be used to monitor the activities of the employees for example, the system may detect the time between orders being transmitted and goods being located.

Various other mechanisms can be used to check the operations of the inventive system. In an embodiment, the inventive system may perform periodic connection checks to determine if the system is operating properly. The system check may be the transmission of a beacon which is a check signal transmission between the transceivers and the hangers. The beacon can be various predefined commands. For example, the beacon can be a command from the computer to the hangers to return communication packets back to the computer. The computer can transmit the beacon and then wait for the reply. Alternatively, the beacons can be communication packets that are check signals that are only transmitted from each of the hangers to the computer. The system will listen for the communication packets from each hanger and if the beacon is not received within a predetermined period of time, the system will conclude that communications were lost between the computer and one or more of the hangers. The computer can then perform a reset process. The beacons may be transmitted once every 30 seconds and the system may reset if the communication packets are not received within 60 seconds. The transceiver can facilitate various other modes of operation.

It will be understood that the inventive system has been described with reference to particular embodiments, however additions, deletions and changes could be made to these embodiments without departing from the scope of the inventive system. Although the order filling apparatus and method have been described include various components, it is well understood that these components and the described configuration can be modified and rearranged in various other configurations.

What is claimed is:

1. A product storage apparatus comprising:
   a computer coupled to memory for storing a database that contains hanger addresses associated with a plurality of hangers, the computer having a user interface for the user to enter a request for goods needed by the user and contained on one of the hangers;
   a transmitter coupled to the computer and responsive to the user request for transmitting radio frequency packets that include the hanger addresses associated with requested goods;
   a rail having a first conductor and a second conductor that extends along the length of the rail;
   a power supply coupled to the first conductor and the second conductor; and
   the plurality of hangers, each hanger comprising:
      a hook having a power receiver;
      a rechargeable power supply coupled to the power receiver;
      a microprocessor powered by the rechargeable power supply identified by a hanger address;
      a receiver coupled to the microprocessor for receiving the radio frequency packets sent by the transmitter containing hanger addresses;
      an indicator light that is actuated by the microprocessor when the radio frequency packets containing the hanger address corresponding to the hanger are received; and
      a container for storing goods:
   wherein the indicator light on the hanger containing the goods requested by the user is actuated in response to the hanger receiving the radio frequency packet having the hanger address associated with the request for goods entered by the user at the computer user interface.

2. The product storage apparatus of claim 1, further comprising:
   a plurality of radio frequency transmitters for transmitting radio frequency packets, wherein each of the transmitters is coupled to one of the hangers; and
   a receiver coupled to the computer for receiving the radio frequency packets from the plurality of hangers.

3. The product storage apparatus of claim 1, further comprising:
   a verification receiver that is coupled to the computer for receiving the radio frequency packets from the transmitter coupled to the computer.

4. The product storage apparatus of claim 1, wherein each indicator light can display a plurality of different colors, depending upon the content of the illumination signals in the radio frequency packets sent by the transmitter coupled to the computer.

5. The product storage apparatus of claim 1, wherein each indicator light can be illuminated in a plurality of different flash patterns depending upon the content of the illumination signals in the radio frequency packets sent by the transmitter coupled to the computer.

6. The product storage apparatus of claim 1, further comprising:
   a bar code reader coupled to the computer for reading bar codes marked on each of the hangers.

7. The product storage apparatus of claim 1, further comprising:
   an RFID reader coupled to the computer for reading RFID tags coupled to the hangers.

8. The product storage apparatus of claim 1, further comprising:
   a biometric reader coupled to the computer for verifying an identity of a recipient.

9. The product storage apparatus of claim 1, wherein for the plurality of hangers, each hanger further comprises a transceiver which includes the receiver.

10. The product storage apparatus of claim 1, wherein the power receiver includes a first contact for connection to the first conductor of the rail and a second contact for connection to the second conductor of the rail.

11. The product storage apparatus of claim 9, wherein the first conductor is a first conductive strip and the second conductor is a second conductive strip.

12. The product storage apparatus of claim 1, wherein the power receiver includes a charging inductive coil.

13. The product storage apparatus of claim 11, wherein the rail includes primary inductive coils coupled to the first conductor and the second conductor and a mechanism to align the charging inductive coil with one of the primary inductive coils.

14. The product storage apparatus of claim 11, wherein the rail includes a primary inductive coil that extends along the length of the rail and is coupled to the first conductor and the second conductor.

* * * * *

UNITED STATES PATENT AND TRADEMARK OFFICE
CERTIFICATE OF CORRECTION

PATENT NO. : 8,355,962 B2  
APPLICATION NO. : 12/196078  
DATED : January 15, 2013  
INVENTOR(S) : Kevin C. Delaney et al.

It is certified that error appears in the above-identified patent and that said Letters Patent is hereby corrected as shown below:

On the Title page of the letters patent under the item number (75) for Inventors Names and Places of Residence, change Inventor "William S. Cras, Alamo, CA (US);" to --William S. Criss, Alamo, CA (US);--.

On the Title page of the letters patent under the item number (75) for Inventors Names and Places of Residence, change Inventor "David A. Victoria, Blackton, CA (US)" to --David A. Valencia, Stockton, CA (US)--.

Signed and Sealed this  
Nineteenth Day of November, 2013

Teresa Stanek Rea  
*Deputy Director of the United States Patent and Trademark Office*